United States Patent
Chiang et al.

[11] Patent Number: 5,928,153
[45] Date of Patent: Jul. 27, 1999

[54] ULTRASOUND FLOW VELOCITY AND DOPPLER ANGLE MEASUREMENT METHOD AND SYSTEM

[75] Inventors: Hui-Hua Chiang, 3F, 11, Lane 69, Tien-Mou E. Road; Bor-Ray Lee, both of Taipei, Taiwan

[73] Assignee: Hui-Hua Chiang, Taipei, Taiwan

[21] Appl. No.: 09/198,348

[22] Filed: Nov. 24, 1998

[51] Int. Cl.⁶ ..................................................... A61B 8/00
[52] U.S. Cl. ............................................ 600/454; 600/455
[58] Field of Search .................................. 600/443, 454, 600/455, 456, 465, 453

[56] References Cited

U.S. PATENT DOCUMENTS

| | | | |
|---|---|---|---|
| 5,148,808 | 9/1992 | Satake | 600/454 |
| 5,409,010 | 4/1995 | Beach et al. | 600/454 |

*Primary Examiner*—Marvin M. Lateef
*Assistant Examiner*—Maulin Patel
*Attorney, Agent, or Firm*—Smith, Gambrell & Russell, LLP; Beveridge, DeGrandi, Weilacher & Young Intellectual Property Group

[57] ABSTRACT

An ultrasound flow velocity and Doppler angle measurement method and system is provided for measuring the velocity and direction of a flow, such as the blood flow in a human body, in a non-contact manner through ultrasound means. In practical applications, this ultrasound flow velocity measurement method and system can be utilized, for example, in the field of physiological diagnosis for blood-flow velocity measurement to determine whether the patient suffers from blood vessel disorders, such as embolism and aneurysm. Precise measurement can be achieved through the use of just one set of ultrasound transducer in the system configuration; therefore, this ultrasound flow velocity measurement method and system is simpler in system configuration and more cost-effective to use than the prior art. Experimentation shows that the estimation has a standard deviation of less than 4.5° for Doppler angle range from 45° to 80°. Therefore, the measurement results are trustworthy to use.

14 Claims, 4 Drawing Sheets

ULTRASOUND FLOW VELOCITY AND DOPPLER ANGLE MEASUREMENT METHOD AND SYSTEM

BACKGROUND OF THE INVENTION

1. Field of the Invention

This invention relates to ultrasound measurement technology, and more particularly, to an ultrasound method and system which is capable of measuring the velocity of a flow, such as the blood flow in a human body, in a non-contact manner through ultrasound means. In practical applications, the invention can be utilized, for example, in the field of physiological diagnosis for blood-flow velocity measurement to determine whether the patient suffers from blood vessel disorders, such as embolism and aneurysm.

2. Description of Related Art

The Doppler effect is a widely utilized natural law in many various scientific and technical applications. The Doppler principle states that when a wave, either sound or radio, is scattered back from a target with relative motion to the source, the observed frequency of the scattering wave is higher than the source frequency if the target is moving toward the source, and lower than the source frequency if the target is moving away from the source. Accordingly, the velocity of a moving target can be detected by directing a wave at the target and then measuring the observed frequency of the scattering wave from the target.

The Doppler effect is a well known principle to all learned people in the field of science and technology, so detailed description thereof will not be further given. In the filed of physiological diagnosis, for instance, the Doppler effect can be used for the measurement of blood-flow velocity in human blood vessels. If the blood, low velocity at a particular point in a blood vessel is abnormal, it can be concluded that patient may be suffering from blood vessel disorders, such as embolism or aneurysm.

FIG. 1A is a schematic diagram used to depict the application of the ultrasound Doppler effect for blood-flow velocity measurement. As shown, an ultrasound beam 10 is controllably directed at a selected measurement point P in a human blood vessel 20. In accordance with the Doppler equation:

$$f_d = \frac{2 \cdot v}{\lambda} \cdot \cos\theta \quad (A1)$$

where $f_d$ is the mean value of all the frequency components in the Doppler spectrum (for reasons that will be explained later, the peak-intensity frequency rather than the mean frequency will be used by the invention);

v is the blood-flow velocity at the measurement point P;

$\lambda$ is the wavelength of the ultrasound beam 10; and $\theta$ is the Doppler angle between the emitting direction of the ultrasound beam 10 and the blood-flow velocity vector $\vec{v}$ at the measurement point P.

If the resulted Doppler spectrum is symmetrical in form; the mean frequency $f_d$ of the Doppler spectrum would be equal to the peak-intensity frequency $f_{peak}$ (also referred to as energy peak frequency); whereas, if asymmetrical, the peak-intensity frequency $f_{peak}$ would represent the velocity of the majority of the particles in the flow. Since the Doppler spectrum would be asymmetrical in most cases, the peak-intensity frequency $f_{peak}$ rather than the mean frequency $f_d$ would be the predominant frequency in the Doppler equation. Therefore, Eq. (A1) can be rewritten as:

$$f_{peak} = \frac{2 \cdot v}{\lambda} \cdot \cos\theta \quad (A2)$$

The relationship of Eq. (A2) is herein and hereinafter referred to as "Doppler-Spectrum Peak-Intensity Frequency Equation" throughout this specification.

From Eq. (A2), it can be deduced that $$v = \frac{f_{peak} \cdot \lambda}{2 \cdot \cos\theta} \quad (A3)$$

Accordingly, the magnitude of the blood-flow velocity v can be determined if the values of $f_{peak}$, $\lambda$, and $\theta$ are all known. The value of $f_{peak}$ can be acquired from the Doppler spectrum, and the value of $\lambda$ is inherent to the ultrasound beam 10 being used and thus can be known in advance.

A conventional method for determining the Doppler angle $\theta$ involves the use of a manually movable and rotatable marker on the monitor screen that displays an ultrasound scan image. The operator can move and rotate the marker through manual control to visually align the marker in parallel with the extending direction of the blood vessel where the measurement point is located. The angle between the marker and the ultrasound beam is then taken as the Doppler angle $\theta$. This marker method, however, has the following two drawbacks.

First, since the blood vessels in a human body are mostly curved and extend in all directions with very few straight segments, the manual control of the marker would be very difficult to achieve precise alignment with the blood vessel. The blood-flow velocity measurement can therefore be imprecise. This drawback is schematically depicted in FIG. 1B. As shown, if the measurement point P is located in a curved segment of the blood vessel 20, then it would be highly difficult for the operator to visually align the marker in parallel with the blood-flow velocity vector $\vec{v}$ at the measurement point P. The result of the blood-flow velocity measurement is therefore highly untrustworthy.

Second, in a 2-D (two-dimensional) ultrasound scan image, the marker method to find the Doppler angle would be unfeasible if the blood vessel 20 is unparalleled to the scanning plane. To make alignment possible, the scanning plane should be first aligned in parallel with the extending direction of the blood vessel 20. This requirement, however, is difficult to achieve for most internal blood vessels.

If the obtained Doppler angle is imprecise, the subsequently obtained blood-flow velocity v0 from Eq. (A3) will be also imprecise. A conventional solution to this problem involves the use of two sets of ultrasound transducers for 2-D Doppler angle measurement, and three sets for 3-D Doppler angle measurement. This solution, however, is quite complex in system configuration and costly to implement due to the need to use two or more sets of ultrasound transducers.

Through research, Newhouse et al. have found that, if a focusable ultrasound beam with a circular emitting plane (i.e., the ultrasound beam is conically shaped and symmetrical in form about its propagation axis) is used as the ultrasound source, then the band-width $B_d$ of the Doppler spectrum can be formulated as follows:

$$B_d = \frac{2v}{\lambda} \cdot \frac{W}{F} \cdot \sin\theta \qquad (A4)$$

where v is the blood-flow velocity at the measurement point;

$\lambda$ is the wavelength of the ultrasound beam;

W is the diameter of the circular emitting plane of the ultrasound beam;

F is the focusing length of the ultrasound beam (i.e., the distance between the focal point and the emitting plane of the ultrasound beam); and $\theta$ is the Doppler angle between the ultrasound beam and the blood-flow velocity vector.

Theoretically, the maximum Doppler frequency $f_{max}$ in the Doppler spectrum is defined as the frequency component at the upper bound of the bandwidth $B_d$ and which is equal to the peak-intensity Doppler frequency $f_{peak}$ plus half of the bandwidth $B_d$, i.e.,.

$$f_{max} = f_{peak} + B_d/2 \qquad (A5)$$

Moreover, Newhouse and Tortoli have jointly found that the maximum Doppler frequency $f_{max}$ can be formulated as follows:

$$f_{max} = \frac{2v}{\lambda} \cdot \cos\theta + \frac{v}{\lambda} \cdot \frac{W}{F} \cdot \sin\theta \qquad (A6)$$

The relationship of Eq. (A6) is herein and hereinafter referred to as "Newhouse-Tortoli Maximum Doppler Frequency Equation" throughout this specification.

Detailed discussions about the equations Eqs. (A4), (A5) and (A6) can be found in the following technical publications:

(1) "Three-dimensional Vector Flow Estimation Using Two Transducers and Spectral Width", IEEE Trans. Ultra. Ferro. Freq. Con., Vol. 41, pp.90–95, 1994, by V. L. Newhouse, K. S. Dickerson, D. Cathignol, and J. Y. Chapelon;

(2) "Ultrasound Doppler Probing of Flows Transverse with Respect to Beam Axis", IEEE Trans. Biomed. Eng., Vol. BME-34, pp.779–789, 1987, by V. L. Newhouse, D. Censor, T. Vontz, J. A. Cisneros, and B. B Goldberg; and (3) "Theory of Ultrasound Doppler-Spectral Velocimetry for Arbitrary Beam and Flow Configurations", IEEE Trans. Biomed. Eng., Vol. BME-35, pp.740–751, 1988, by D. Censor, V. L. Newhouse, and T. Vontz.

Based on the findings disclosed in these papers, the inventors propose a new ultrasound method and system for measuring the velocity and direction of a flow, such as a blood flow in a human body.

SUMMARY OF THE INVENTION

It is an objective of the present invention to provide a new ultrasound flow velocity measurement method and system, which can achieve precise measurement through the use of just one set of ultrasound transducer in the system configuration.

It is another objective of the present invention to provide a new ultrasound flow velocity measurement method and system, which is easier and more convenient to operate than the prior art.

It is still another objective of the present invention to provide a new ultrasound flow velocity measurement method and system, which is more cost-effective to install and use than the prior art.

In accordance with the foregoing and other objectives of the present invention, a new ultrasound flow velocity measurement method and system is provided. The method and system of the invention can be implemented with existing ultrasound Doppler system using an annular-array transducer or a 2-D phased-array transducer.

By the invention, the ultrasound flow velocity measurement method and system utilized a ultrasound transducer capable of generating an ultrasound beam of a fixed wavelength and having a circular emitting plane of a fixed diameter and a known focusing length. In operation, the ultrasound beam is first focused at the measurement point to obtain the Doppler spectrum of the backscattering ultrasound waves from the measurement point. The Doppler spectrum is preferably obtained from the averaging of a number of successively acquired sets of spectrum data for the purpose of noise reduction. The peak-intensity Doppler frequency component and the maximum Doppler frequency component (the upper bound of the bandwidth of the Doppler spectrum) of the Doppler spectrum are then acquired. Next, the magnitude of the Doppler angle is determined in accordance with the Chiang-Lee's Doppler Angle Estimation Equation, while the magnitude of the flow velocity is determined in accordance with the Chiang-Lee's Flow Velocity Estimation Equation. The Chiang-Lee's Doppler Angle Estimation Equation and the Chiang-Lee's Flow Velocity Estimation Equation are the results of the solution to the simultaneous equation set of the Doppler-Spectrum Peak-Intensity Frequency Equation and the Newhouse-Tortoli Maximum Doppler Frequency Equation. Finally, the magnitude of the Doppler angle and the magnitude of the flow velocity are displayed in human-cognizable form on a display unit, such as a digital display or a computer monitor screen.

Experimentation shows that the estimation has a standard deviation of less than 4.5° for Doppler angle range from 45° to 80°, which is close to or better than the prior art that uses manually-set marker to determine the Doppler angle. The measurement results are acceptable and trustworthy.

BRIEF DESCRIPTION OF DRAWINGS

The invention can be more fully understood by reading the following detailed description of the preferred embodiments, with reference made to the accompanying drawings, wherein.

DETAILED DESCRIPTION OF PREFERRED EMBODIMENTS

A preferred embodiment of the ultrasound flow velocity measurement method and system according to the invention is disclosed in full details in the following with reference to FIGS. 2, 3, 4 and 5A–5C.

In the following preferred embodiment of the invention, the ultrasound flow velocity measurement method and system is utilized in the field of physiological diagnosis for blood-flow velocity measurement in human blood vessels. However, it should be understood that the invention is not limited to such an application. Broadly speaking, the invention can be used to measure the velocity of a flowing stream of fluid that can scatter ultrasound waves incident thereon, such as blood and bubble water, but excluding water since water is non-scattering to ultrasound waves.

System Configuration

Figure 1A:
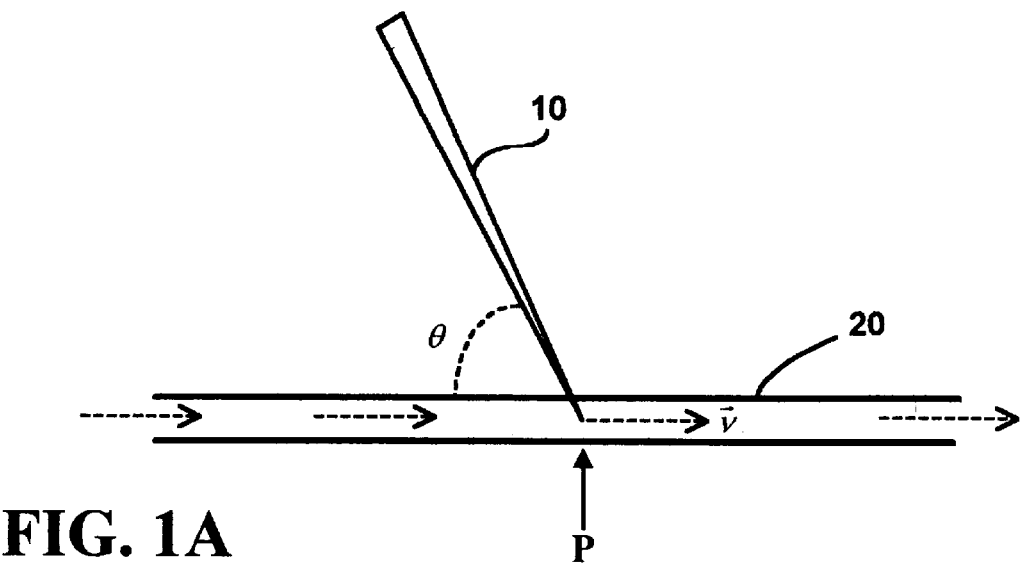
FIG. 1A is a schematic diagram used to depict the application of the ultrasound Doppler effect for blood-flow velocity measurement.
Figure 1B:
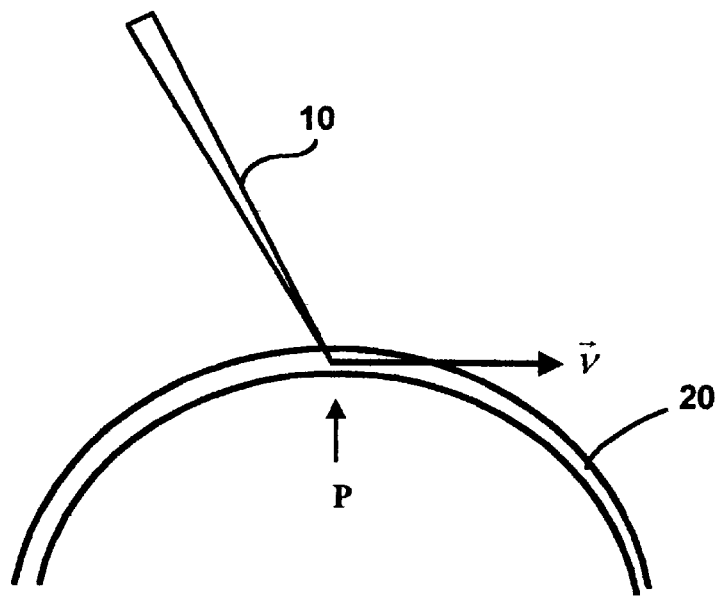
FIG. 1B is a schematic diagram used to explain the drawback of using a conventional ultrasound method for blood-flow velocity measurement.
Figure 2:
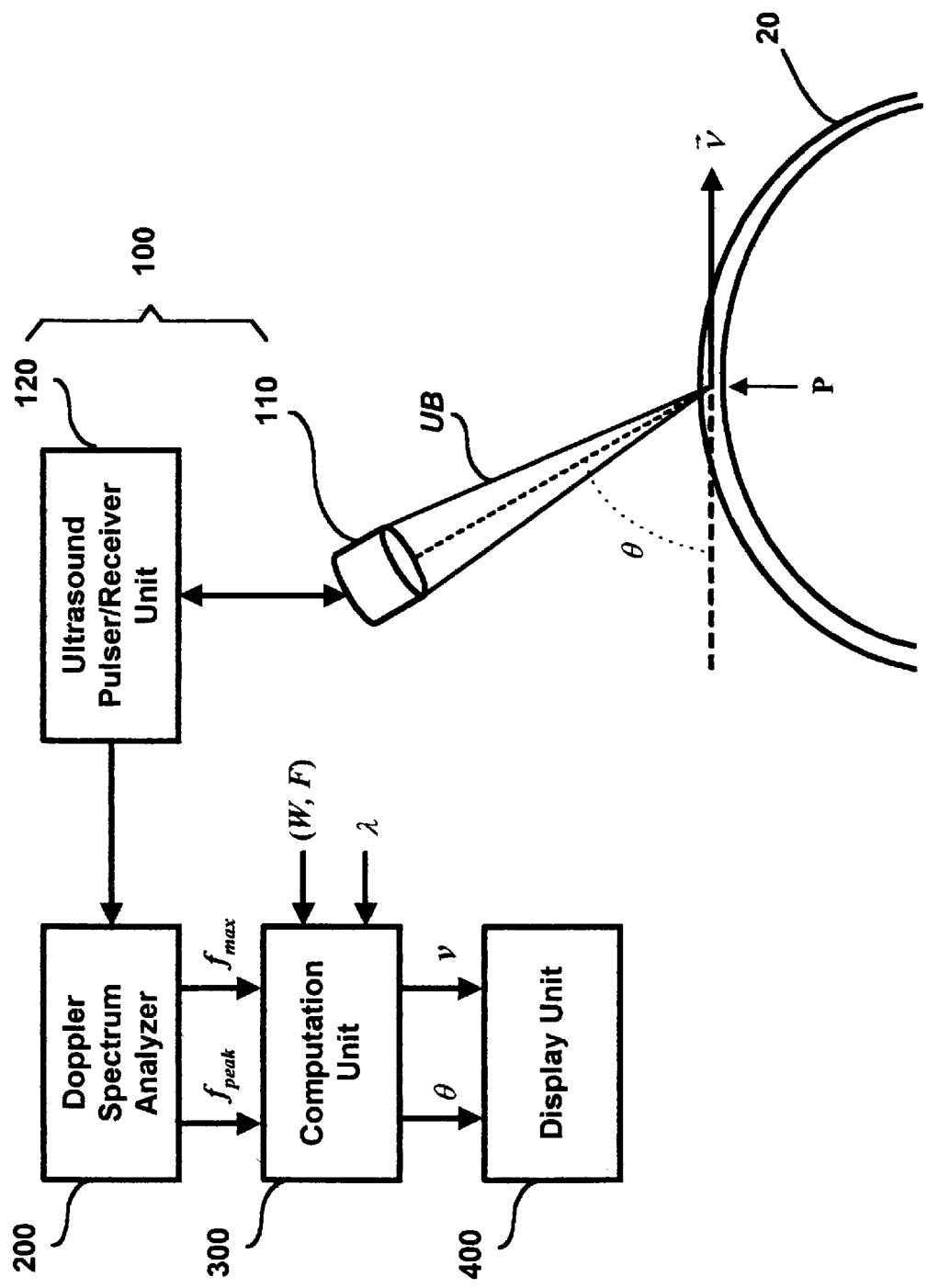
FIG. 2 is a schematic block diagram showing the system configuration of the ultrasound flow velocity measurement method and system according to the invention.

FIG. 2 is a schematic block diagram showing the system configuration of the ultrasound flow velocity measurement method and system according to the invention. As shown, the method and system of the invention includes an ultrasound apparatus 100 (which is composed of an ultrasound transducer 110 and an ultrasound pulser/receiver unit 120), an ultrasound Doppler spectrum analyzer 200, a computation unit 300, and a display unit 400. In this preferred embodiment, for example, this ultrasound flow velocity measurement method and system is used to measure the blood-flow velocity v at an arbitrarily selected measurement point P in a human blood vessel 20.

The ultrasound transducer 110 is capable of generating a focusable ultrasound beam UB, which can be controllably directed to focus at the selected measurement point P. The ultrasound pulser/receiver unit 120 is an integrated part to the ultrasound transducer 110, and which is used to drive the generation of the ultrasound beam UB from the ultrasound transducer 110 and is capable of receiving the backscattering ultrasound waves from the measurement point P. The Doppler spectrum analyzer 200 is used to produce the Doppler spectrum of backscattered ultrasound signal from the pulser/receiver unit 120.

It is an important aspect of the invention that the focusable ultrasound beam UB generated by the ultrasound transducer 110 should have a circular emitting plane having a fixed diameter and can be focused at any selected measurement point in the blood vessel 20. Available types of ultrasound transducers that meet this requirement include, for example, the annular-array type of ultrasound transducer and the 2-D phased-array type of ultrasound transducer.

Figure 3:
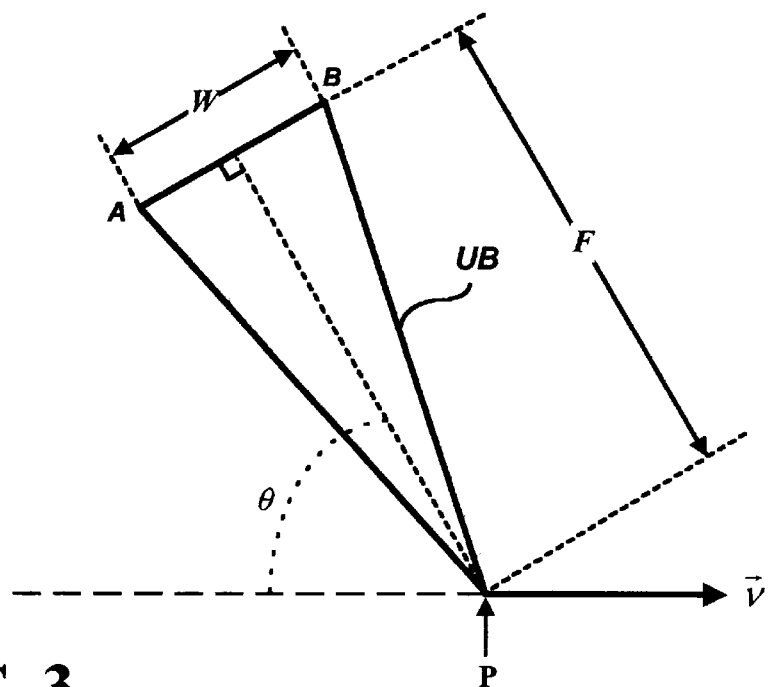
FIG. 3 is a geometric representation of the longitudinal sectional view of the ultrasound beam utilized in the method and system of the invention.

FIG. 3 is a geometric representation of a longitudinal sectional view of the ultrasound beam UB when being focused at the selected measurement point P in the blood vessel 20. Since the ultrasound beam UB is symmetrically shaped about its propagation axis, any longitudinal sectional view of the ultrasound beam UB is triangularly shaped, as the triangle ΔPAB shown in FIG. 3.

Assume that the diameter of the circular emitting plane of the ultrasound beam UB, which is represented by the line segment $\overline{AB}$, is denoted by W; and the focusing length (i.e., the distance between the measurement point P and the emitting plane of the ultrasound beam UB) is denoted by F. Further, assume that the blood-flow velocity at the measurement point P is v, and the Doppler angle between the propagation axis of the ultrasound beam UB and the blood-flow velocity vector $\vec{v}$ at the measurement point P is denoted by θ. The values of W and F are both preknown.

When the ultrasound beam UB is scattered back by the blood flow at the measurement point P, the backscattering ultrasound waves are received by the ultrasound apparatus 100 where the backscattering ultrasound waves are converted into electrical signals and then transferred to the Doppler spectrum analyzer 200 for analysis.

Ultrasound Doppler Spectrum

The Doppler spectrum analyzer 200 is capable of computing the Doppler spectrum from the electrical signals and then analyzing the Doppler spectrum in a specific manner described in the following with reference to FIG. 4.

Figure 4:
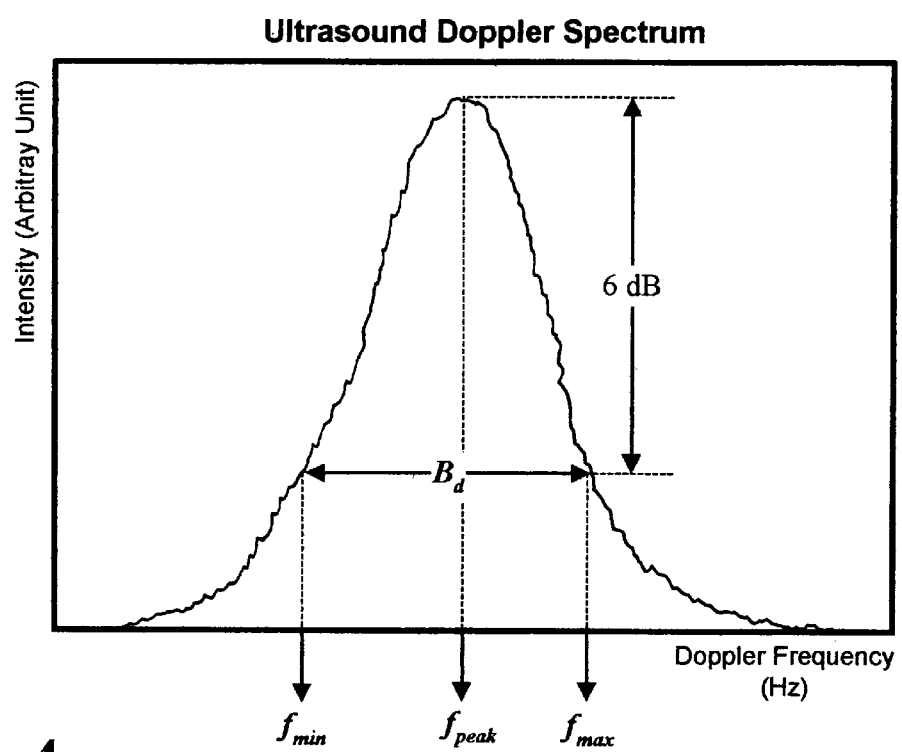
FIG. 4 is a graph showing a Doppler spectrum obtained by the method and system of the invention.

FIG. 4 is a graph showing the ultrasound Doppler spectrum displayed on the Doppler spectrum analyzer 200. As shown, the Doppler spectrum has a bandwidth $B_d$ with an upper bound at $f_{max}$ (referred to as the maximum Doppler frequency) and a lower bound at $f_{min}$ (referred to as the minimum Doppler frequency). Moreover, the peak intensity in the Doppler spectrum appears at $f_{peak}$ (referred to as the peak-intensity Doppler frequency). The Doppler spectrum analyzer 200 is capable of automatically acquiring the values of the peak-intensity Doppler frequency $f_{peak}$ and the maximum Doppler frequency $f_{max}$ from the Doppler spectrum.

The bandwidth $B_d$ of the Doppler spectrum is theoretically formulated in the equation shown in Eq. (A4); the peak-intensity Doppler frequency $f_{peak}$ is theoretically formulated in the Doppler-Spectrum Peak-Intensity Frequency Equation shown in Eq. (A2), and the maximum Doppler frequency $f_{max}$ is theoretically formulated in the Newhouse-Tortoli Maximum Doppler Frequency Equation shown in Eq. (A6).

In practice, however, the low-frequency portion of the Doppler spectrum (i.e., the portion to the left of the peak-intensity Doppler frequency $f_{peak}$ shown in FIG. 4) would be somewhat filtered out by the wall-thump filter used in the ultrasound pulser/receiver unit 120 and also dependent on the size and volume of the flow being measured. For this reason, the low-frequency portion of the Doppler spectrum will not be used in the blood-flow velocity estimation; in other words, the minimum Doppler frequency $f_{min}$, which lies within the low-frequency portion of the Doppler spectrum, will not be used. Moreover, since the mean Doppler frequency $f_d$ is obtained by averaging all the frequency components including those in the low-frequency portion of the Doppler spectrum, the peak-intensity Doppler frequency $f_{peak}$ rather than the mean Doppler frequency $f_d$ will be used in the blood flow velocity estimation. Therefore, from the Doppler spectrum, only the peak-intensity Doppler frequency $f_{peak}$ and the maximum Doppler frequency $f_{max}$ are used to determine the Doppler angle θ and the blood-flow velocity v.

Doppler Spectrum Noise Reduction

Due to the fact that the acquired Doppler spectrum would contain noises from various sources in the ultrasound system, it is required to use noise-reduction technique to reduce the noise effect. The most commonly used spectrum noise-reduction method is the averaging technique, which can reduce the noise effect by averaging a number of successively obtained sets of spectrum data. In practice, however, a blood flow may either be a constant flow or a pulsating flow. In the case of constant flow, the velocity and direction (i.e., Doppler angle) thereof are both time-invariant. Therefore, a number of successively obtained sets of spectrum data from the constant flow are also time-invariant and thus can be directly averaged for noise reduction. In the case of pulsating flow, however, since the flow velocity is time-variant (assuming the time-variant flow velocity is denoted by v(t)), then Eqs. (A2) and (A6) can be rewritten as:

$$f_{peak} = \frac{2 \cdot v(t)}{\lambda} \cdot \cos\theta \qquad (B1)$$

$$f_{max} = \frac{2v(t)}{\lambda} \cdot \cos\theta + \frac{v(t)}{\lambda} \cdot \frac{W}{F} \cdot \sin\theta \qquad (B2)$$

Since the parameters ($\lambda$, $\theta$, W, F) are substantially constant, Eq. (B2) can be rewritten as:

$$f_{max} = K \cdot v(t) \qquad (B3)$$

where K is a constant, and $$K = \frac{2}{\lambda} \cdot \left( \cos\theta + \frac{W}{2F} \cdot \sin\theta \right)$$

Assume two successively sets of Doppler spectrum data are obtained, which are respectively represented by Spectrum_1 and Spectrum_2, then $$f_{max\_1} = K \cdot v_1(t)$$

and $$f_{max\_2} = K \cdot v_2(t)$$

where $f_{max\_1}$ is the maximum Doppler frequency of Spectrum_1;

$v_1(t)$ is the instant flow velocity at the time the measurement of Spectrum_1 is taken;

$f_{max\_2}$ is the maximum Doppler frequency of Spectrum_2; and $v_2(t)$ is the instant flow velocity at the time the measurement of Spectrum_2 is taken.

Hence, $$\frac{f_{max\_1}}{f_{max\_2}} = \frac{K \cdot v_1(t)}{K \cdot v_2(t)} = \frac{v_1(t)}{v_2(t)} = R \qquad (B4)$$

where R represents the ratio of the maximum Doppler frequency of Spectrum_1 to that of Spectrum_2, and can be used as a normalizing factor to perform frequency normalization between Spectrum_1 and Spectrum_2.

As mentioned earlier, the high-frequency part of Doppler spectrum would be less susceptible to noise than the low-frequency part, and therefore, the maximum Doppler frequency rather than the peak-intensity Doppler frequency is used in the normalization. A Doppler-spectrum normalization process on a number of successively obtained sets of Doppler spectrum data is schematically depicted in FIGS. 5A–5C.

Figure 5A:
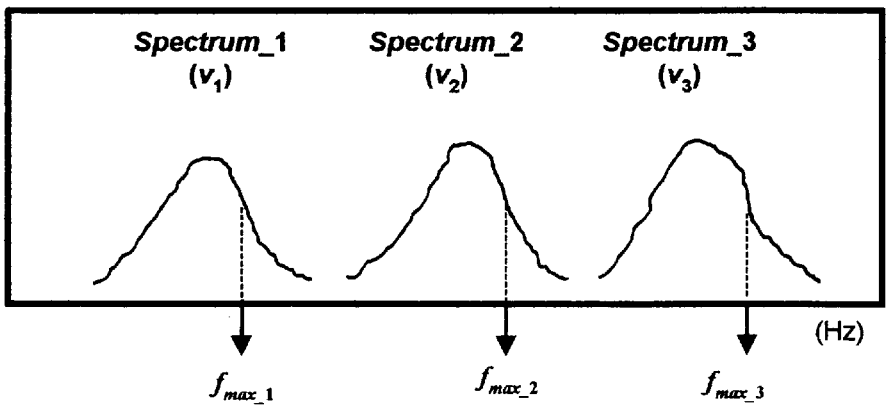
FIGS. 5A–5C are schematic diagrams used to depict a Doppler-spectrum normalization process and an averaging process on a number of sets of Doppler spectrum data.
Figure 5B:
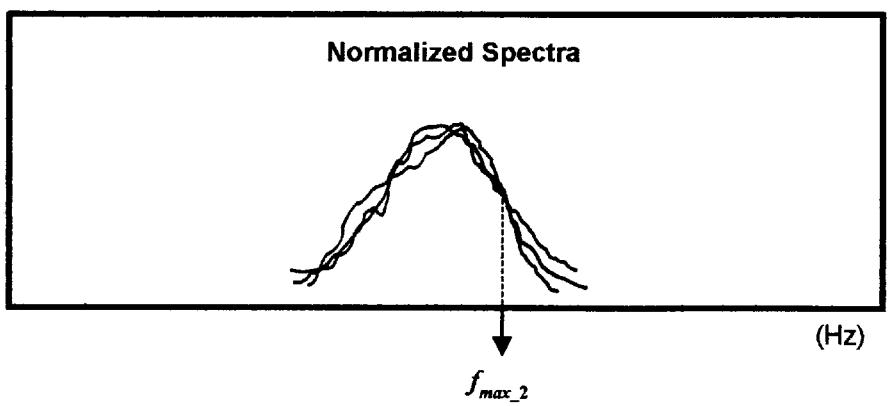
Figure 5C:
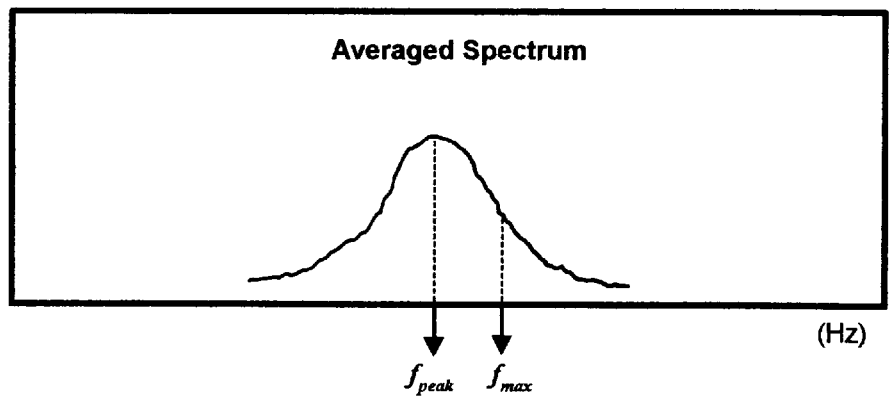

As shown in FIG. 5A, assume three sets of Doppler spectrum data, respectively represented by Spectrum_1, Spectrum_2, and Spectrum_3, are obtained from the same measurement point in a pulsating flow measured at different times, and also assume that these three spectra Spectrum_1, Spectrum_2, and Spectrum_3 correspond respectively to the flow velocities $v_1$, $v_2$, and $v_3$. In the first step of the Doppler-spectrum normalization process, the respective maximum Doppler frequencies of the three Doppler spectra are extracted, which are respectively denoted by $f_{max\_1}$, $f_{max\_2}$, and $f_{max\_3}$. Next, assume $v_2$ is to be determined. Then, as shown in FIG. 5B, the other two spectra Spectrum_1 and Spectrum_3 are normalized to Spectrum_2 by respectively scaling $f_{max\_1}$ and $f_{max\_3}$ to $f_{max\_2}$ in accordance with Eq. (B4), i.e., by using the factor $f_{max\_1}/f_{max\_2}$ to normalize Spectrum_1 to Spectrum_2 and the factor $f_{max\_3}/f_{max\_2}$ to normalize Spectrum_3 to Spectrum_2. Subsequently, as shown in FIG. 5C, an averaging process is performed to average the three normalized spectra into a single spectrum. Through this averaging process, noise reduction can be achieved. The averaged Doppler spectrum is then used for acquisition of the maximum Doppler frequency $f_{max}$ and the peak-intensity Doppler frequency $f_{peak}$.

The foregoing Doppler-spectrum normalization process and averaging process in the spectrum noise-reduction method are all performed by the Doppler spectrum analyzer 200.

Calibration Process

Since the ultrasound apparatus 100 can be realized from various models, each having its own particular electrical and gain characteristics, a calibration process is preferably performed in advance to calibrate for the bandwidth of the Doppler spectrum. The calibration process is performed on a flow phantom with a selected set of known Doppler angles, such as (50°, 60°, 70°) for the purpose of calibrating for a threshold used to determine the maximum Doppler frequency $f_{max}$. This allows the maximum Doppler frequency $f_{max}$ to be more precisely obtained when performing the measurement.

Computation and Display

From the simultaneous equation set of the Doppler-Spectrum Peak-Intensity Frequency Equation shown in Eq. (A2) and the Newhouse-Tortoli Maximum Doppler Frequency Equation shown in Eq. (A6), the following equations can be deduced:

$$\theta = \tan^{-1}\left( \frac{f_{max} - f_{peak}}{f_{peak}} \cdot \frac{2 \cdot F}{W} \right) \qquad (B5)$$

$$v = \sqrt{\left( \frac{\lambda \cdot f_{peak}}{2} \right)^2 + \left[ \frac{\lambda \cdot F}{W} \cdot (f_{max} - f_{peak}) \right]^2} \qquad (B6)$$

The relationship of Eq. (B5) is herein and hereinafter referred to as "Chiang-Lee's Doppler Angle Estimation Equation" throughout this specification; while the relationship of Eq. (B6) is herein and hereinafter referred to as "Chiang-Lee's Flow Velocity Estimation Equation" throughout this specification It can seen that, of the seven variables ($f_{peak}$, $f_{max}$, $\lambda$, W, F, $\theta$, v) in Eqs. (B5) and (B6), ($\lambda$, W, P) are preknown and ($f_{peak}$, $f_{max}$) are acquired from the Doppler spectrum. Therefore, the values of ($\theta$, v) can be determined simply by plugging the values of ($f_{peak}$, $f_{max}$, $\lambda$, W, F) into Eqs. (B5) and (B6).

The computation processes for $\theta$ and v in accordance with Eqs. (B5) and (B6) are implemented by the computation unit 300, which can be either a specifically designed digital circuit or a standalone computer running a software program that implements Eqs. (B5) and (B6). Of the known parameters ($\lambda$, W, F) and ($f_{peak}$, $f_{max}$), the parameters ($\lambda$, W, F) are preset to the computation unit 300, while the parameters ($f_{peak}$, $f_{max}$) are furnished by the Doppler spectrum analyzer 200. The computation results are then transferred to the display unit 400, which can be, for example, a digital display or a computer monitor, so as to display the magnitudes of the Doppler angle $\theta$ and the blood-flow velocity v in human-cognizable form.

Conclusion

Experimentation shows that the estimation has a standard deviation of less than 4.5° fbr Doppler angle range from 45° to 80°. Therefore, the measurement results are trustworthy to use.

In conclusion, the ultrasound flow velocity measurement method and system of the invention has the following advantages over the prior art. First, the method and system of the invention needs to use just one set of ultrasound transducer, thus making the overall system configuration less complex than the prior art. The method and system of the invention is therefore more convenient and cost-effective to use than the prior art. Second, the ultrasound transducer utilized in the method and system of the invention can be the widely used annular-array type of ultrasound transducer without having to design a dedicated one. The method and system of the invention is therefore easy to implement.

The invention has been described using exemplary preferred embodiments. However, it is to be understood that the scope of the invention is not limited to the disclosed embodiments. On the contrary, it is intended to cover various modifications and similar arrangements. The scope of the claims, therefore, should be accorded the broadest interpretation so as to encompass all such modifications and similar arrangements.

What is claimed is:

1. A method for measuring the velocity and direction of a flow at a selected measurement point, comprising the steps of:
    (1) focusing an ultrasound beam of a fixed wavelength and a known focusing length at the measurement point, the ultrasound beam being emitted from a circular emitting plane of a fixed diameter and being symmetrical in form about its propagation axis;
    (2) obtaining the Doppler spectrum of the backscattering ultrasound waves from the measurement point;
    (3) from the Doppler spectrum, finding the peak-intensity Doppler frequency and the maximum Doppler frequency thereof;
    (4) from the Chiang-Lee's Doppler Angle Estimation Equation, computing for the Doppler angle of the ultrasound beam, the Doppler angle being the angle between the propagation axis of the ultrasound beam and the flow direction;
    from the Chiang-Lee's Flow Velocity Estimation Equation, computing for the velocity of the flow at the measurement point; and
    (5) displaying the magnitude of the Doppler angle and the magnitude of the flow velocity at the measurement point in human-cognizable form.

2. The method of claim 1, wherein the ultrasound beam is generated by an annular-array type of ultrasound transducer.

3. The method of claim 1, wherein the ultrasound beam is generated by a 2-D phased-array type of ultrasound transducer.

4. The method of claim 1, further comprising, prior to said step (1), the step of:
    performing a calibration process with a selected set of known Doppler angles to calibrate for a threshold used to determine the maximum Doppler frequency of the Doppler spectrum.

5. The method of claim 1, wherein in said step (2), the Doppler spectrum is an averaged Doppler spectrum obtained through the steps of:
    (2-1) obtaining a number of successively acquired sets of Doppler spectrum data from the backscattering ultrasound waves from the measurement point;
    (2-2) from each of the obtained sets of Doppler spectrum data, obtaining the maximum Doppler frequency thereof;
    (2-3) performing a Doppler-spectrum normalization process to normalize all the obtained sets of Doppler spectrum data to a selected spectrum by scaling the maximum Doppler frequency of each spectrum to the selected one; and
    (2-4) performing an averaging process to average all the normalized sets of Doppler spectrum data to thereby obtain the averaged Doppler spectrum.

6. A method for measuring the velocity and direction of a blood flow at a selected measurement point in a blood vessel, comprising the steps of:
    (1) focusing an ultrasound beam of a fixed wavelength and a known focusing length at the measurement point, the ultrasound beam being emitted from a circular emitting plane of a fixed diameter and being symmetrical in form about its propagation axis;
    (2) obtaining the Doppler spectrum of the backscattering ultrasound waves from the measurement point;
    (3) from the Doppler spectrum, finding the peak-intensity Doppler frequency and the maximum Doppler frequency thereof;
    (4) from the Chiang-Lee's Doppler Angle Estimation Equation, computing for the Doppler angle of the ultrasound beam, the Doppler angle being the angle between the propagation axis of the ultrasound beam and the flow direction;
    from the Chiang-Lee's Flow Velocity Estimation Equation, computing for the velocity of the blood flow at the measurement point; and
    (5) displaying the magnitude of the Doppler angle and the magnitude of the blood flow velocity at the measurement point in human-cognizable form.

7. The method of claim 6, wherein the ultrasound beam is generated by an annular-array type of ultrasound transducer.

8. The method of claim 6, wherein the ultrasound beam is generated by a 2-D phased-array type of ultrasound transducer.

9. The method of claim 6, further comprising, prior to said step (1), the step of:
    performing a calibration process with a selected set of known Doppler angles to calibrate for a threshold used to determine the maximum Doppler frequency of the Doppler spectrum.

10. The method of claim 6, wherein in said step (2), the Doppler spectrum is an averaged Doppler spectrum obtained through the steps of:
    (2-1) obtaining a number of successively acquired sets of Doppler spectrum data from the backscattering ultrasound waves from the measurement point;
    (2-2) from each of the obtained sets of Doppler spectrum data, obtaining the maximum Doppler frequency thereof;
    (2-3) performing a Doppler-spectrum normalization process to normalize all the obtained sets of Doppler spectrum data to a selected spectrum by scaling the maximum Doppler frequency of each spectrum to the selected one; and
    (2-4) performing an averaging process to average all the normalized sets of Doppler spectrum data to thereby obtain the averaged Doppler spectrum.

11. An ultrasound system for measuring the velocity and direction of a blood flow at a selected measurement point in a blood vessel, which comprises:
    (a) an ultrasound apparatus including an ultrasound pulser/receiver unit and an ultrasound transducer;
    the ultrasound transducer having a circular emitting plane of a fixed diameter for emitting an ultrasound beam of a fixed wavelength and a known focusing length, and which is capable of focusing the ultrasound beam at the measurement point; and the ultrasound pulser/receiver unit being capable of acquiring the Doppler spectrum of the backscattering ultrasound waves from the measurement point;

(b) a Doppler spectrum analyzer, which receives the data of the Doppler spectrum from the ultrasound apparatus and is capable of finding the peak-intensity Doppler frequency component and the maximum Doppler frequency component of the Doppler spectrum;

(c) a computation unit, which receives the acquired data of the peak-intensity Doppler frequency and the maximum Doppler frequency from the Doppler spectrum analyzer and is capable of computing for the Doppler angle of the ultrasound beam in accordance with the Chiang-Lee's Doppler Angle Estimation Equation, the Doppler angle being the angle between the propagation axis of the ultrasound beam and the flow direction; and computing for the velocity of the blood flow at the measurement point in accordance with the Chiang-Lee's Flow Velocity Estimation Equation; and (d) a display unit for displaying the magnitude of the Doppler angle and the magnitude of the flow velocity in human-cognizable form.

12. The ultrasound system of claim 11, wherein the ultrasound transducer is an annular-array type of ultrasound transducer.

13. The ultrasound system of claim 11, wherein the ultrasound transducer is a 2-D phased-array type of ultrasound transducer.

14. The ultrasound system of claim 11, wherein the Doppler spectrum analyzer uses an averaged Doppler spectrum to obtain the maximum Doppler frequency and the peak-intensity Doppler frequency, with the averaged Doppler spectrum being obtained through the steps of:

(b-1) obtaining a number of successively acquired sets of Doppler spectrum data from the backscattering ultrasound waves from the measurement point;

(b-2) from each of the obtained sets of Doppler spectrum data, obtaining the maximum Doppler frequency thereof;

(b-3) performing a Doppler-spectrum normalization process to normalize all the obtained sets of Doppler spectrum data to a selected spectrum by scaling the maximum Doppler frequency of each spectrum to the selected one; and (b-4) performing an averaging process to average all the normalized sets of Doppler spectrum data to thereby obtain the averaged Doppler spectrum.

* * * * *